United States Patent
Sharma et al.

(10) Patent No.: US 11,983,318 B1
(45) Date of Patent: May 14, 2024

(54) FULL FIELD RETINAL IMAGING SYSTEM FOR CHARACTERIZATION OF EYE TRACKERS

(71) Applicant: Meta Platforms Technologies, LLC, Menlo Park, CA (US)

(72) Inventors: Robin Sharma, Woodinville, WA (US); Nicholas Daniel Trail, Bothell, WA (US); Robert Dale Cavin, Bellevue, WA (US); Kyle Justin Curts, Carnation, WA (US)

(73) Assignee: META PLATFORMS TECHNOLOGIES, LLC, Menlo Park, CA (US)

( * ) Notice: Subject to any disclaimer, the term of this patent is extended or adjusted under 35 U.S.C. 154(b) by 0 days.

(21) Appl. No.: 18/124,945

(22) Filed: Mar. 22, 2023

Related U.S. Application Data (63) Continuation of application No. 16/936,337, filed on Jul. 22, 2020, now Pat. No. 11,635,807, which is a continuation of application No. 15/896,330, filed on Feb. 14, 2018, now Pat. No. 10,761,602.

(60) Provisional application No. 62/471,247, filed on Mar. 14, 2017.

(51) Int. Cl.
*G02B 27/01* (2006.01)
*G02B 27/00* (2006.01)
*G06F 3/01* (2006.01)

(52) U.S. Cl.
CPC ......... *G06F 3/013* (2013.01); *G02B 27/0093* (2013.01); *G02B 2027/0138* (2013.01); *G02B 2027/014* (2013.01); *G02B 27/0172* (2013.01)

(58) Field of Classification Search
CPC ............................ G06F 3/013; G02B 27/0093
USPC ......................................... 351/205–206, 210
See application file for complete search history.

(56) References Cited

U.S. PATENT DOCUMENTS

| 5,233,373 | A | 8/1993 | Peters et al. |
| 7,637,615 | B2 | 12/2009 | Yamada |
| 8,777,413 | B2 * | 7/2014 | Zhou ............. A61B 3/103 351/221 |
| 8,964,298 | B2 | 2/2015 | Haddick et al. |

(Continued)

OTHER PUBLICATIONS

Sheehy C., et al., "High-Speed, Image-Based Eye Tracking with a Scanning Laser Ophthalmoscope," Biomedical Optics Express, Oct. 1, 2012, vol. 3 (10), pp. 2611-2622.

(Continued)

*Primary Examiner* — James R Greece
(74) *Attorney, Agent, or Firm* — Mannava & Kang, P.C.

(57) ABSTRACT

A retinal imaging system includes a projector, an imaging device, and a controller coupled to an eye tracking system under test. The projector emits a light pattern to be delivered to a pupil of an eye, a location of the pupil being estimated by the eye tracking system under test. The imaging device captures one or more images of a retina of the eye illuminated with at least a portion of the light pattern. The controller determines one or more eye tracking parameters based on the captured one or more images of the retina. The controller compares each determined eye tracking parameter with each of estimated one or more eye tracking parameters, wherein values for the one or more eye tracking parameters are estimated by the eye tracking system under test. The controller characterizes each estimated eye tracking parameter based on the comparison.

20 Claims, 7 Drawing Sheets

(56) References Cited

U.S. PATENT DOCUMENTS

| | | | |
|---|---|---|---|
| 2007/0252951 A1* | 11/2007 | Hammer | A61B 3/103 351/221 |
| 2009/0244482 A1* | 10/2009 | Elsner | A61B 3/1025 351/206 |
| 2009/0316115 A1 | 12/2009 | Itoh et al. | |
| 2010/0053555 A1 | 3/2010 | Enriquez et al. | |
| 2011/0299034 A1 | 12/2011 | Walsh et al. | |
| 2011/0307216 A1 | 12/2011 | Lindquist | |
| 2012/0105486 A1 | 5/2012 | Lankford et al. | |
| 2012/0147326 A1 | 6/2012 | Yatagai et al. | |
| 2013/0178287 A1 | 7/2013 | Yahav | |
| 2014/0055337 A1 | 2/2014 | Karlsson | |
| 2014/0098198 A1 | 4/2014 | Lee et al. | |
| 2014/0163329 A1 | 6/2014 | Brown, Jr. et al. | |
| 2014/0361996 A1 | 12/2014 | Eden et al. | |
| 2015/0331485 A1 | 11/2015 | Wilairat et al. | |
| 2016/0134863 A1 | 5/2016 | Horesh | |
| 2016/0139665 A1 | 5/2016 | Lopez et al. | |
| 2016/0216761 A1 | 7/2016 | Klingstrom et al. | |
| 2016/0342205 A1 | 11/2016 | Shigeta et al. | |
| 2017/0065171 A1 | 3/2017 | Satake et al. | |
| 2017/0090562 A1 | 3/2017 | Gustafsson et al. | |
| 2017/0316264 A1 | 11/2017 | Gustafsson et al. | |
| 2019/0094981 A1 | 3/2019 | Bradski et al. | |
| 2019/0129501 A1 | 5/2019 | Nistico et al. | |

OTHER PUBLICATIONS

Yang Q., et al., "Design of an Integrated Hardware Interface for AOSLO Image Capture and Cone-Targeted Stimulus Delivery," Optics Express, Aug. 16, 2010, vol. 18 (17), pp. 17841-17858.

Yang Y., et al., "Assessing Sodium Iodate Induced Outer Retinal Changes in Rats Using Confocal Scanning Laser Ophthalmoscopy and Optical Coherence Tomography," Investigative Opthalmology & Visual Science, 2014, vol. 55 (3), pp. 1696-1705.

* cited by examiner

FULL FIELD RETINAL IMAGING SYSTEM FOR CHARACTERIZATION OF EYE TRACKERS

CROSS-REFERENCE TO RELATED APPLICATIONS

This application is a continuation of U.S. application Ser. No. 16/936,337, filed Jul. 22, 2020, which is a continuation of U.S. application Ser. No. 15/896,330, filed Feb. 14, 2018, now U.S. Pat. No. 10,761,602, which claims the benefit of U.S. Provisional Patent Application Ser. No. 62/471,247, filed Mar. 14, 2017, all of which are hereby incorporated by reference in their entirety.

TECHNICAL FIELD

The present disclosure generally relates to eye tracking, and specifically relates to a full field retinal imaging system for characterization of eye trackers.

BACKGROUND

Eye tracking refers to the process of detecting the direction of a user's gaze, which may comprise detecting the angular orientation of the eye in three-dimensional space. Eye tracking may further comprise detecting the location of the eye (e.g., the center of the eye), the torsion (i.e., the roll of the eye about the pupillary axis) of the eye, the shape of the eye, the current focal distance of the eye, the dilation of the pupil, other features of the eye's state, or some combination thereof.

Eye tracking is an important feature for various systems used in artificial reality applications, e.g., head-mounted display (HMD) systems. Conventional eye tracking systems track features of the human eye and are typically limited by the quality of the optical path. These conventional systems do not provide sufficient accuracy needed for eye tracking in a HMD system.

SUMMARY

A retinal imaging system for characterizing performance of an eye tracking system under test is presented herein. The retinal imaging system includes a projector, an imaging device, and a controller coupled to the eye tracking system under test. The projector is configured to emit a light pattern to deliver light to at most a pupil of a user's eye. A location of the pupil may be estimated by the eye tracking system under test and provided to the controller of the retinal imaging system. The imaging device is configured to capture one or more images of a retina of the eye, wherein at least a portion of the light pattern reaches the retina. The controller determines one or more eye tracking parameters based on the captured one or more images of the retina. The eye tracking system under test estimates values for the one or more eye tracking parameters either concurrently with determination of the one or more eye tracking parameters by the retinal imaging system, or sequentially. The controller compares each of the determined eye tracking parameters and each of the estimated eye tracking parameters. The controller characterizes each of the estimated eye tracking parameters based on the comparison. By characterizing the estimated eye tracking parameters, the retinal imaging system characterizes performance of the eye tracking system under test.

After the retinal imaging system characterizes performance of the eye tracking system under test, the eye tracking system under test may be integrated into a head-mounted display (HMD). The HMD displays content to a user wearing the HMD. The HMD may be part of an artificial reality system. The HMD may further include an electronic display and an optical assembly. The electronic display is configured to emit image light. The optical assembly is configured to provide optical correction to the image light and direct the image light to an eye-box of the HMD corresponding to a location of a user's eye determined by the integrated eye tracking system.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Embodiments of the present disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

A full field retinal imaging system is configured to characterize performance of an eye tracking system under test that may be later incorporated into a HMD. The HMD may be part of an artificial reality system. The eye tracking system under test provides an estimated location of a user's pupil to the retinal imaging system. The retinal imaging system delivers light to the user's pupil based on the estimated pupil location. The retinal imaging system includes an illumination source that comprises, e.g., a two-dimensional (2D) array of light emitting diodes (LEDs) that render content to the user's pupil. The retinal imaging system further includes an imaging device (camera) that captures images of the rendered content on the user's retina over a relatively large field-of-view (e.g., 45 degrees). The retinal imaging system determines one or more eye tracking parameters (e.g., gaze angle) using the captured images. The eye tracking system under test concurrently monitors a position and orientation of the user's eye. The eye tracking system under test estimates values for the one or more eye tracking parameters and provides the estimated values to the retinal imaging system. The retinal imaging system compares the determined eye tracking parameters with the estimated eye tracking parameters to characterize performance of the eye tracking system under test.

Figure 1:
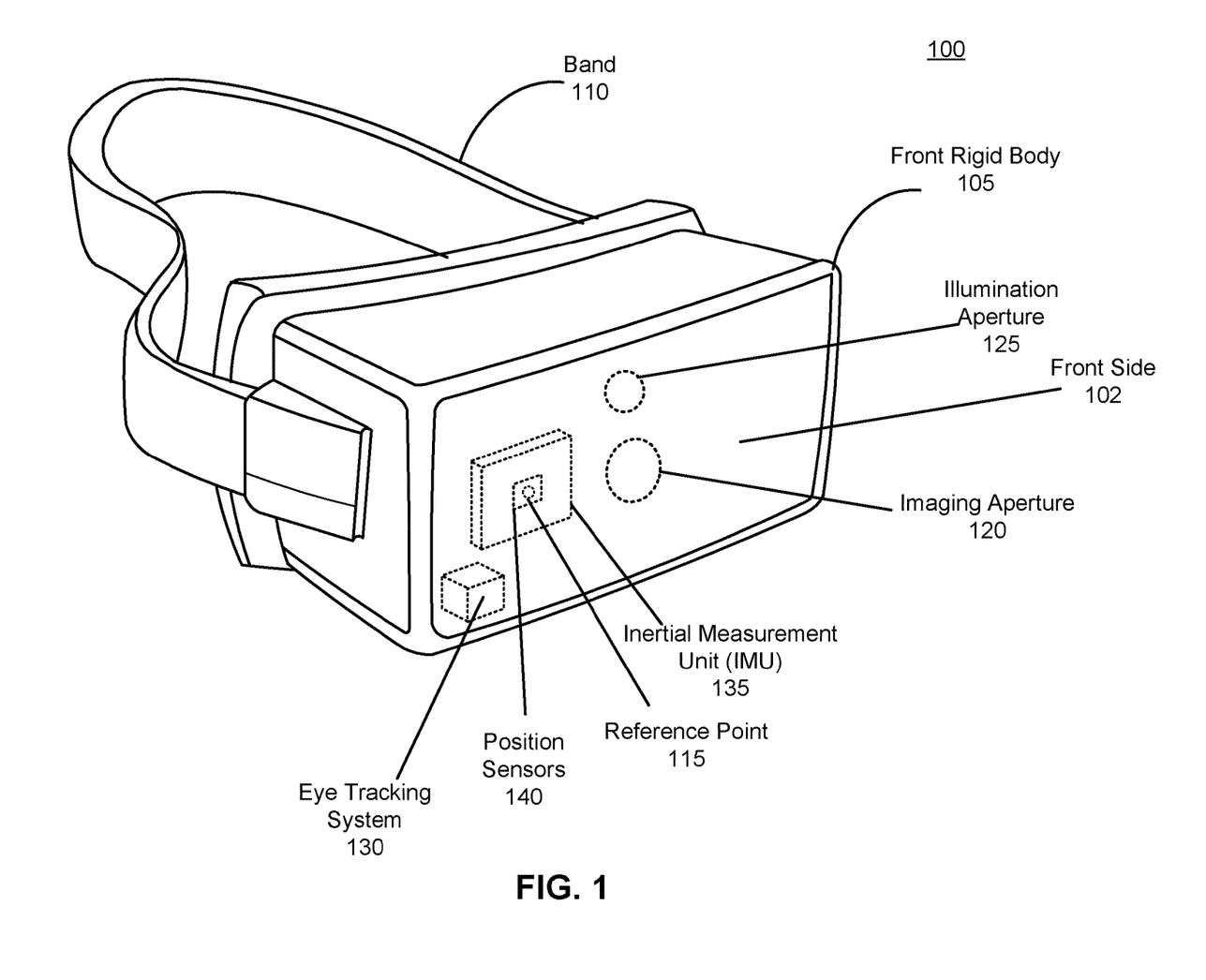
FIG. 1 is a diagram of a head-mounted display (HMD), in accordance with one or more embodiments.

FIG. 1 is a diagram of a HMD 100, in accordance with one or more embodiments. The HMD 100 may be part of an artificial reality system. In embodiments that describe AR system and/or a MR system, portions of a front side 102 of the HMD 100 are at least partially transparent in the visible band (~380 nm to 750 nm), and portions of the HMD 100 that are between the front side 102 of the HMD 100 and an eye of the user are at least partially transparent (e.g., a partially transparent electronic display). The HMD 100 includes a front rigid body 105, a band 110, and a reference point 115. In some embodiments, the HMD 100 shown in FIG. 1 also includes a depth camera assembly (DCA) configured to determine depth information of a local area surrounding some or all of the HMD 100. In these embodiments, the HMD 100 would also include an imaging aperture 120 and an illumination aperture 125, and an illumination source of the DCA would emit light through the illumination aperture 125. The illumination source may be composed of a plurality of laser-type light emitters on a single substrate configured to simultaneously or in different time instants emit a plurality of light beams, e.g., in the form of a structured light pattern. An imaging device of the DCA would capture light from the illumination source that is reflected/scattered from the local area through the imaging aperture 120. A controller coupled to the imaging device or integrated within the imaging device of the DCA determines depth information of the one or more objects in the local area based on the captured reflected/scattered light. The same or a separate controller can control operation of the illumination source of the DCA.

In one embodiment, the front rigid body 105 includes one or more electronic display elements (not shown in FIG. 1), one or more integrated eye tracking systems 130 (e.g., one eye tracking system 130 for each eye of a user wearing the HMD 100), an Inertial Measurement Unit (IMU) 135, one or more position sensors 140, and the reference point 115. In the embodiment shown by FIG. 1, the position sensors 140 are located within the IMU 135, and neither the IMU 135 nor the position sensors 140 are visible to a user of the HMD 100. The IMU 135 is an electronic device that generates fast calibration data based on measurement signals received from one or more of the position sensors 140. A position sensor 140 generates one or more measurement signals in response to motion of the HMD 100. Examples of position sensors 140 include: one or more accelerometers, one or more gyroscopes, one or more magnetometers, another suitable type of sensor that detects motion, a type of sensor used for error correction of the IMU 135, or some combination thereof. The position sensors 140 may be located external to the IMU 135, internal to the IMU 135, or some combination thereof. The one or more electronic display elements of the HMD 100 may be integrated into an electronic display (not shown in FIG. 1). The electronic display generates image light. In some embodiments, the electronic display includes an optical element that adjusts the focus of the generated image light. The electronic display displays images to the user in accordance with data received from a console (not shown in FIG. 1). In various embodiments, the electronic display may comprise a single electronic display or multiple electronic displays (e.g., a display for each eye of a user). Examples of the electronic display include: a liquid crystal display (LCD), an organic light emitting diode (OLED) display, an inorganic light emitting diode (ILED) display, an active-matrix organic light-emitting diode (AMOLED) display, a transparent organic light emitting diode (TOLED) display, some other display, a projector, or some combination thereof. The electronic display may also include an aperture, a Fresnel lens, a convex lens, a concave lens, a diffractive element, a waveguide, a filter, a polarizer, a diffuser, a fiber taper, a reflective surface, a polarizing reflective surface, or any other suitable optical element that affects the image light emitted from the electronic display. In some embodiments, one or more of the display block optical elements may have one or more coatings, such as anti-reflective coatings.

The HMD 100 may also include an optical assembly (not shown in FIG. 1). The optical assembly magnifies received light from the electronic display, corrects optical aberrations associated with the image light, and the corrected image light is presented to a user of the HMD 100. At least one optical element of the optical assembly may be an aperture, a Fresnel lens, a refractive lens, a reflective surface, a diffractive element, a waveguide, a filter, a reflective surface, a polarizing reflective surface, or any other suitable optical element that affects the image light emitted from the electronic display. Moreover, the optical assembly may include combinations of different optical elements. In some embodiments, one or more of the optical elements in the optical assembly may have one or more coatings, such as anti-reflective coatings, dichroic coatings, etc. Magnification of the image light by the optical assembly allows elements of the electronic display to be physically smaller, weigh less, and consume less power than larger displays. Additionally, magnification may increase a field of view of the displayed media. For example, the field of view of the displayed media is such that the displayed media is presented using almost all (e.g., 110 degrees diagonal), and in some cases all, of the user's field of view. In some embodiments, the optical assembly is designed so its effective focal length is larger than the spacing to the electronic display, which magnifies the image light projected by the electronic display. Additionally, in some embodiments, the amount of magnification may be adjusted by adding or removing optical elements.

The eye tracking system 130 estimates a position and angular orientation of an eye of a user wearing the HMD 100. The position and angular orientation of the eye corresponds to the direction of the user's gaze within the HMD 100. The orientation of the user's eye is defined herein as the direction of the foveal axis, which is the axis between the fovea (an area on the retina of the eye with the highest concentration of photoreceptors) and the center of the eye's pupil. In general, when user's eyes are fixed on a point, the foveal axes of the user's eyes intersect that point. The pupillary axis is another axis of the eye which is defined as the axis passing through the center of the pupil which is perpendicular to the corneal surface. The pupillary axis does not, in general, directly align with the foveal axis. Both axes intersect at the center of the pupil, but the orientation of the foveal axis is offset from the pupillary axis by approximately −1° to 8° laterally and ±4° vertically. Because the foveal axis is defined according to the fovea, which is located in the back of the eye, the foveal axis can be difficult or impossible to detect directly in some eye tracking embodiments. Accordingly, in some embodiments, the orientation of the pupillary axis is detected and the foveal axis is estimated based on the detected pupillary axis.

In general, movement of an eye corresponds not only to an angular rotation of the eye, but also to a translation of the eye, a change in the torsion of the eye, and/or a change in shape of the eye. The eye tracking system 130 may also detect translation of the eye: i.e., a change in the position of the eye relative to the eye socket. In some embodiments, the translation of the eye is not detected directly, but is approximated based on a mapping from a detected angular orientation. Translation of the eye corresponding to a change in the eye's position relative to the detection components of the eye tracking system 130 may also be detected. Translation of this type may occur, for example, due to shift in the position of the HMD 100 on a user's head. The eye tracking system 130 may also detect the torsion of the eye, i.e., rotation of the eye about the pupillary axis. The eye tracking system 130 may use the detected torsion of the eye to estimate the orientation of the foveal axis from the pupillary axis. The eye tracking system 130 may also track a change in the shape of the eye, which may be approximated as a skew or scaling linear transform or a twisting distortion (e.g., due to torsional deformation). The eye tracking system 130 may estimate the foveal axis based on some combination of the angular orientation of the pupillary axis, the translation of the eye, the torsion of the eye, the current shape of the eye, an accommodation of the eye, etc.

The eye tracking system 130 provides for means to relate an exterior three-dimensional surface of cornea and sclera in the eye to its gaze position, in addition to an optical power through the front corneal surface and interaction with the pupil surface. The sclera is the relatively opaque (usually visibly white) outer portion of the eye, which is often referred to as the "white of the eye." The cornea is the curved surface covering the iris and the pupil of the eye. The eye tracking system 130 allows for a path to measure eye surfaces/features off-axis (from the direct pupil gaze) through one or more sensing methods.

As the orientation and position may be determined for both eyes of the user, the eye tracking system 130 is able to determine where the user is looking. The HMD 100 can use the orientation and position of the eye to, e.g., determine an inter-pupillary distance (IPD) of the user, determine gaze direction, introduce depth cues (e.g., blur image outside of the user's main line of sight), collect heuristics on the user interaction in the artificial reality media (e.g., time spent on any particular subject, object, or frame as a function of exposed stimuli), some other function that is based in part on the orientation of at least one of the user's eyes, or some combination thereof. Determining a direction of a user's gaze may include determining a point of convergence based on the determined orientations of the user's left and right eyes. A point of convergence may be the point that the two foveal axes of the user's eyes intersect (or the nearest point between the two axes). The direction of the user's gaze may be the direction of a line through the point of convergence and though the point halfway between the pupils of the user's eyes.

The eye tracking system 130 can be positioned between the user's eye and the optical assembly. In alternate embodiments, the eye tracking system 130 is placed between the optical assembly and the electronic display or within the optical assembly. The eye tracking system 130 may include an illumination source, an imaging device, and a controller coupled to the imaging device or integrated into the imaging device (not shown in FIG. 1). The illumination source emits light onto a portion of the user's eye. The imaging device captures light reflected from the portion of the eye illuminated by the illumination source. The controller may be configured to determine eye tracking information for the user's eye. The eye tracking information determined by the eye tracking system 130 may comprise information about a position and orientation of the user's eye in an eye-box, such as information about a location of a pupil of the eye and information about an angle of eye-gaze. An eye-box represents a three-dimensional (3D) volume at an output of the HMD 100 in which the user's eye is located to receive image light.

In some embodiments, the components of the eye tracking system 130 are positioned outside an optical axis of the front rigid body 105, i.e., the illumination source and the imaging device are positioned outside of a primary optical path of the electronic display, whether a transmitted or reflected primary optical path of the electronic display. Instead, the illumination source and the imaging device are coupled through one or more non-primary direct or reflected optical paths to the user's eye. The one or more non-primary optical paths may encompass at least part of the primary optical path of the electronic display.

Based on the determined and tracked position and orientation of the user's eye, the HMD 100 may adjust presentation of one or more images displayed on the electronic display. In one embodiment, the HMD 100 may adjust resolution of the displayed image(s) based on the eye tracking information. A maximum pixel density for displaying the image(s) on the electronic display can be provided only in a foveal region of the determined eye-gaze, whereas a lower resolution display is employed in other regions, without negatively affecting the user's visual experience. In another embodiment, the HMD 100 may adjust focus of the displayed image(s) such that the displayed image(s) are in focus at the determined eye-gaze location, which also mitigates vergence-accommodation conflict (VAC) of image light propagating towards the user's eye. The HMD 100 may perform various other applications based at least in part on the determined eye tracking information. The applications include, but are not limited to, providing user interfaces (e.g., gaze-based selection), attention estimation (e.g., for user safety), different gaze-contingent display modes (e.g., synthetic depth of field rendering), metric scaling for depth and parallax correction (e.g., IPD and eye-box adjustment), etc.

Performance of the eye tracking system 130 may be characterized before incorporating the eye tracking system 130 into the HMD 100. Embodiments of the present disclosure support characterizing performance of the eye tracking system 130 before fabrication of the HMD 100 and integration of the eye tracking system 130 into the HMD 100. Performance of the eye tracking system 130 can be characterized by a full field retinal imaging system. The retinal imaging system captures images of content presented on a retina of the user's eye, thus providing the "ground truth" for one or more eye tracking parameters, such as an angle of eye-gaze, a torsion of the user's eye, a shape of the user's eye, a current focal distance of the user's eye, a dilation of a pupil of the user's eye, a translation of the user's eye, an IPD, an accommodation of the user's eye, etc. Details about characterization of the eye tracking system 130 performed before incorporating the eye tracking system 130 into the HMD 100 are further described below in conjunction with FIG. 2, FIGS. 3A-3D and FIG. 4.

Figure 2:
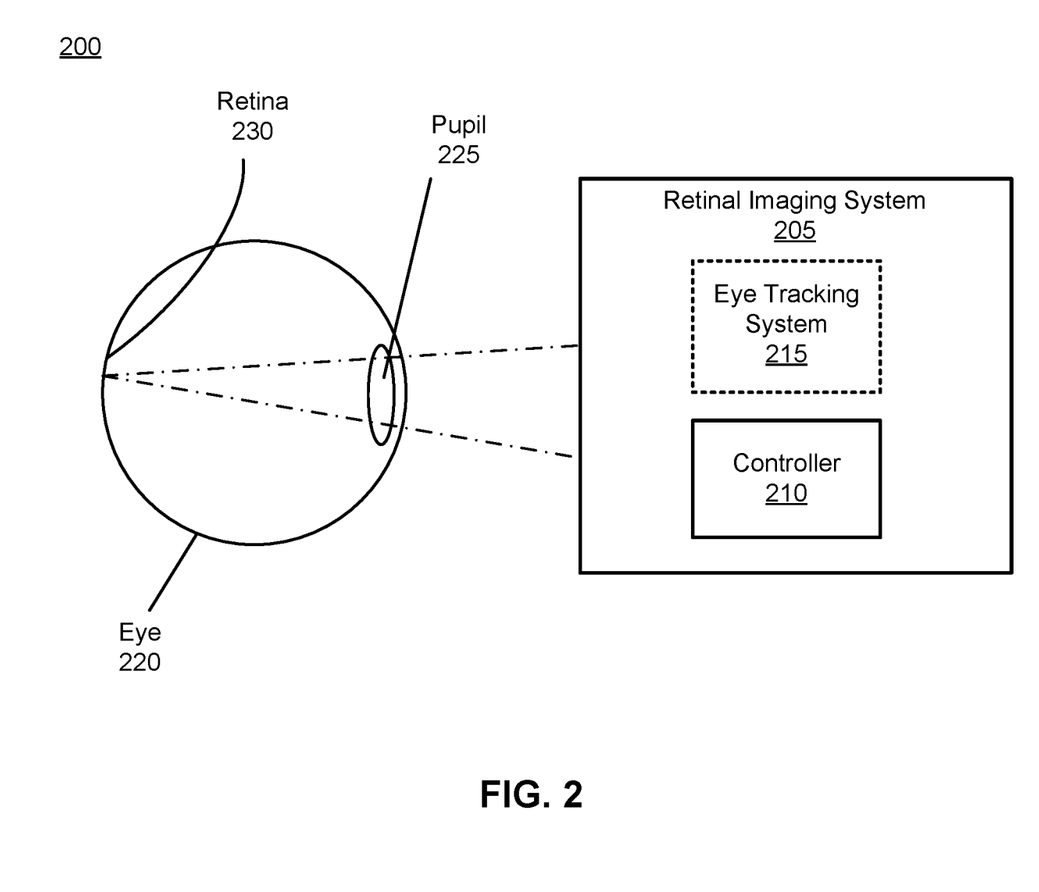
FIG. 2 is a block diagram of a retinal imaging system, which may characterize performance of an eye tracking system under test, in accordance with one or more embodiments.

FIG. 2 is a block diagram 200 of a retinal imaging system 205, in accordance with one or more embodiments. The retinal imaging system 205 includes a controller 210 that may be coupled to an eye tracking system 215 under test. As discussed in more detail in conjunction with FIGS. 3A-3D, the eye tracking system 215 under test is coupled to the retinal imaging system 205 such that the eye tracking system 215 under test and the retinal imaging system 205 can illuminate surfaces of a user's eye 220 and capture images of the surfaces during a specific time period. To operate during the same time period, the retinal imaging system 205 and the eye tracking system 215 under test can utilize different wavelengths of light. Alternatively, the retinal imaging system 205 and the eye tracking system 215 under test can operate at different times while using same or different wavelength(s) of light. The retinal imaging system 205 can be configured to characterize performance of the eye tracking system 215 under test, which may be later incorporated through a fabrication process into a HMD, e.g., the HMD 100 in FIG. 1. The eye tracking system 215 under test may be an embodiment of the eye tracking system 130, which can be integrated after a fabrication process into the HMD 100. The controller 210 coupled to the eye tracking system 215 under test may control operations of both the retinal imaging system 205 and the eye tracking system 215 under test. In an alternate embodiment (not shown in FIG. 2), the controller 210 is implemented as a module separate of the retinal imaging system 205 such that the controller 210 interfaces the retinal imaging system 205 and the eye tracking system 215 under test. The controller 210 may be configured to first activate the eye tracking system 215 under test to estimate a location of a pupil 225 of the eye 220. The eye tracking system 215 under test provides information about the estimated location of the pupil 225 to the controller 210, i.e., to the retinal imaging system 205.

The controller 210 may instruct the retinal imaging system 205 to emit light toward the eye 220, based in part on emission instructions. In particular, the controller 210 may instruct an illumination source (not shown in FIG. 2) of the retinal imaging system 205 to deliver light to the pupil 225 of the eye 220, based on the information about the estimated location of the pupil 225 obtained from the eye tracking system 215 under test. Thus, the emission instructions generated by the controller 210 and provided to the retinal imaging system 205 may include the information about the estimated location of the pupil 225. In some embodiments, the light emitted from the illumination source of the retinal imaging system 205 may be spatially modulated based on the information about the estimated location of the pupil 225 to control amplitudes of the emitted light within an eye-box of the eye 220. In one embodiment, a spatial light modulator (not shown in FIG. 2) is coupled to the illumination source of the retinal imaging system 205 to spatially modulate light emitted from the illumination source that reaches various surfaces of the eye 220 including a retina 230, based on the information about the estimated location of the pupil 225. In an alternate embodiment, the controller 210 is configured to spatially modulate light emitted from the illumination source that reaches various surfaces of the eye 220 including the retina 230, based on the information about the estimated location of the pupil 225. Thus, based on the information about the estimated location of the pupil 225 obtained from the eye tracking system 215 under test, the retinal imaging system 205 renders content to the pupil 225 and further to the retina 230 of the eye 220.

The controller 210 may also instruct an imaging device (not shown in FIG. 2) of the retinal imaging system 205 to capture images of the rendered content on the retina 230. Based on the captured images, the controller 210 may determine one or more eye tracking parameters. For example, the one or more eye tracking parameters include, but are not limited to: an angle of eye-gaze, a torsion of the eye 220, a shape of the eye 220, a current focal distance of the eye 220, a dilation of the pupil 225, an IPD, a translation of the eye 220, an accommodation of the eye 220, other features of the eye's state, or some combination thereof. In one embodiment, the controller 210 may instruct the eye tracking system 215 under test to track a position and orientation of the eye 220 in a time period during which the retinal imaging system 205 determines the one or more eye tracking parameters. In this case, the retinal imaging system 205 and the eye tracking system 215 under test operate at different wavelengths of light. In alternate embodiments, the eye tracking system 215 under test can be configured (e.g., by the controller 210) to track a position and orientation of the eye 220 before or after determination of the one or more eye tracking parameters by the retinal imaging system 205, i.e., operations of the eye tracking system 215 under test and of the retinal imaging system 205 can be sequential. Based on the tracked position and orientation of the eye 220, the eye tracking system 215 under test estimates values for the one or more eye tracking parameters and provides the estimated values to the controller 210. The controller 210 may compare the one or more eye tracking parameters determined by the retinal imaging system 205 and the values for the one or more eye tracking parameters estimated by the eye tracking system 215 under test. The controller 210 may characterize performance of the eye tracking system 215 under test based on the comparison.

Figure 3A:
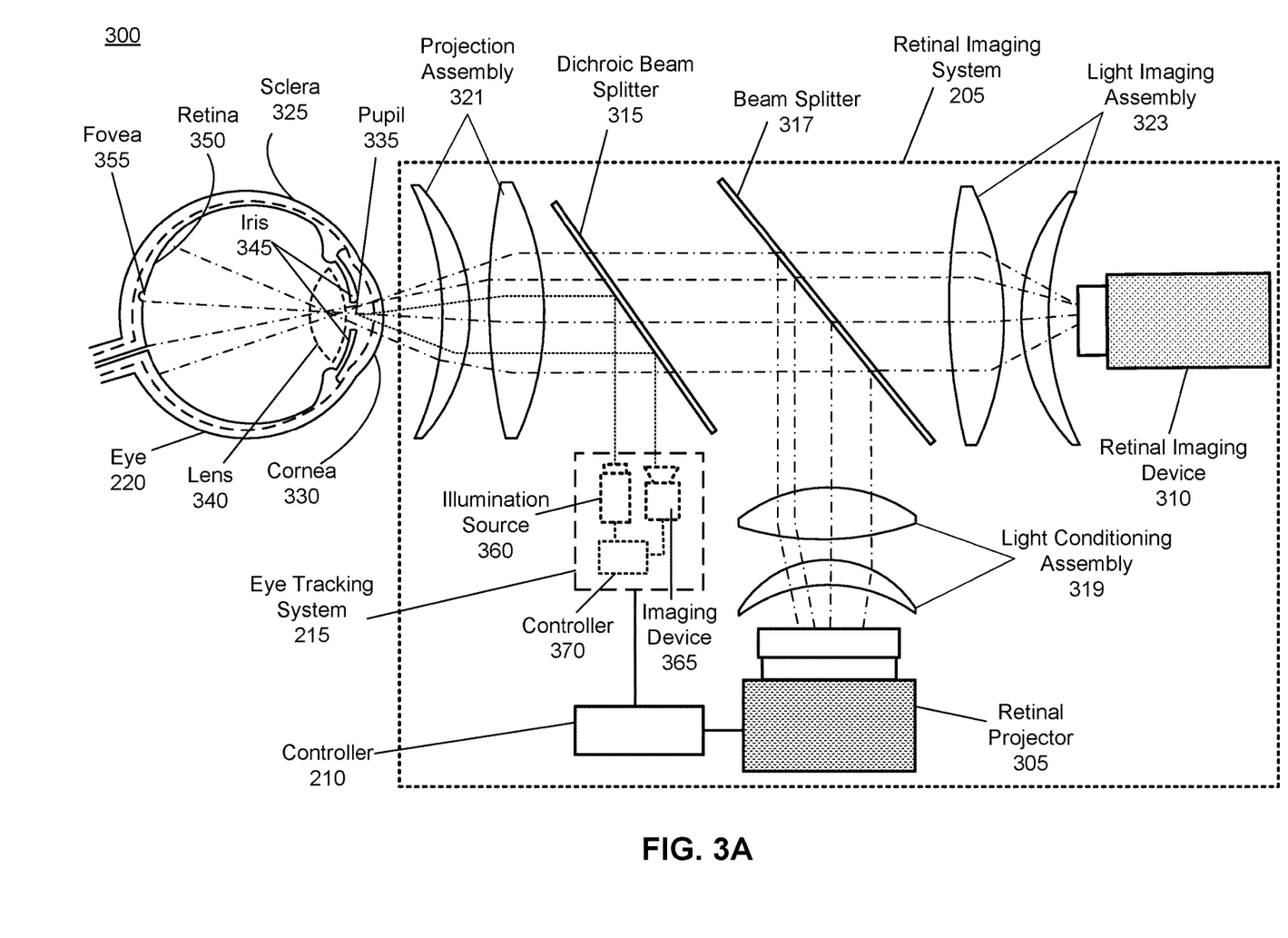
FIG. 3A is a detailed diagram of the retinal imaging system in FIG. 2 that characterizes performance of an eye tracking system under test, which may be later integrated into the HMD in FIG. 1, in accordance with one or more embodiments.

FIG. 3A is a detailed diagram 300 of the retinal imaging system 205 configured to characterize performance of the eye tracking system 215 under test, which may be later incorporated into a HMD (e.g., the HMD 100 in FIG. 1), in accordance with one or more embodiments. As shown in FIG. 3A, the retinal imaging system 205 includes, beside the controller 210, a retinal projector 305, a retinal imaging device 310, a pair of beam splitters 315, 317, a light conditioning assembly 319, a projection assembly 321, and a light imaging assembly 323. In some embodiments, the beam splitter 315 closer to the eye 220 is coated (e.g., with a metal or dichroic coating) to reflect light of one or more wavelengths within a specific range of wavelengths, e.g., infrared (IR) light. The light conditioning assembly 319 may comprise one or more optical elements (lenses), and the light conditioning assembly 319 is configured to generate a conditioned light, e.g., collimating light, expanding light, etc. using light emitted from the retinal projector 305. The projection assembly 321 may comprise one or more optical elements (lenses), and the projection assembly is configured to project light to a particular surface or region of the eye 220. The light imaging assembly 323 may comprise one or more optical elements (lenses) and can be used for focusing, distortion corrections, etc. of image light that is later captured by the retinal imaging device 310.

As shown in FIG. 3A, the eye 220 includes a sclera 325, a cornea 330, a pupil 335, a lens 340, an iris 345, a retina 350, and a fovea 355. The sclera 325 is the relatively opaque (usually visibly white) outer portion of the eye 220, which is often referred to as the "white of the eye." The cornea 330 is the curved surface covering the iris and the pupil of the eye 220. The cornea 330 is essentially transparent in the visible band (~380 nm to 750 nm) of the electromagnetic spectrum, and the near-infrared region (up to approximately 1,400 nanometers). The lens 345 is a transparent structure which serves to focus light at the retina 350 (the back of the eye 220). The iris 345 is a thin, colored, circular diaphragm concentric with the pupil 335. The iris 345 is the colored portion of the eye 220 which contracts to alter the size of the pupil 335, a circular hole through which light enters the eye 220. The fovea 355 is an indent on the retina 350. The fovea 355 corresponds to the area of highest visual acuity, as the fovea 355 is an area on the retina 350 with the highest concentration of photoreceptors.

The eye tracking system 215 under test can be placed into a dedicated slot of the retinal imaging system 205 (not shown in FIG. 3A) coupled to the controller 210. The eye tracking system 215 under test is positioned such that the eye tracking system 215 under test and components of the retinal imaging system 205 can illuminate surfaces of the eye 220 and capture images of the surfaces without interference. To operate during a same time period, the retinal imaging system 205 and the eye tracking system 215 under test utilize different wavelengths of light. Alternatively, the retinal imaging system 205 and the eye tracking system 215 under test can operate at different times while using same or different wavelength(s) of light. The eye tracking system 215 under test shown in FIG. 3A may include an illumination source 360, an imaging device (camera) 365 and a controller 370 that may be coupled to both the illumination source 360 and the imaging device 365. The illumination source 360 is configured to illuminate one or more surfaces of the eye 220, e.g., with IR light. The imaging device 365 is configured to capture light reflected from the one or more surfaces of the eye 220. In an embodiment, the imaging device 365 comprises a camera configured to capture images in the IR. As shown in FIG. 3A, the illumination source 360, the imaging device 365, and the controller 370 are positioned outside of a primary display optical path of the eye 220. A light beam emitted from the illumination source 360 may be reflected as one or more light beams from a surface (e.g., dichroic surface) of the beam splitter 315 toward the eye 220. Light reflected from one or more surfaces of the eye 220 may be further reflected from the surface of the beam splitter 315 toward the imaging device 365.

In some embodiments, the controller 370 estimates a location of the pupil 335 based on light reflected from the pupil 335 and captured by the imaging device 365. The controller 370 is further configured to estimate one or more eye tracking parameters (e.g., an angle of eye-gaze, the torsion of the eye 220, the shape of the eye 220, the current focal distance of the eye 220, the dilation of the pupil 335, other features of the eye's state, or some combination thereof) based on the light reflected from various surfaces of the eye 220 and captured by the imaging device 365. In an alternate embodiment, the eye tracking system 215 under test includes only the imaging device 365, and the controller 370 may be incorporated into the imaging device 365. In this embodiment, light that illuminates one or more surfaces of the eye 220 can be emitted from a display (not shown in FIG. 3A) configured within the retinal imaging system 205 to emit image light toward the eye 220.

In some embodiments, the retinal projector 305 includes a plurality of emitters that each emits light having certain characteristics (e.g., wavelength, polarization, coherence, temporal behavior, etc.). The characteristics may be the same or different between emitters, and the emitters can be operated simultaneously or individually. In one embodiment, the plurality of emitters could be, e.g., laser diodes (e.g., edge emitters), a 2D array of inorganic or organic light emitting diodes (LEDs), a 2D array of vertical-cavity surface-emitting lasers (VCSELs), or some other source. In some embodiments, a single emitter or a plurality of emitters in the retinal projector 305 can emit light having a structured light pattern. In some embodiments, the retinal projector 305 includes a spatial light modulator (not shown in FIG. 3A) that spatially modulates light emitted from the plurality of emitters. As shown in FIG. 3A, the retinal projector 305 and the light conditioning assembly 319 are positioned outside of a primary display optical path of the eye 220. Light emitted from the retinal projector 305 that propagates through the light conditioning assembly 319 is reflected from a surface of the beam splitter 317 and projected by the projection assembly 321 toward the pupil 335 and further to the retina 350.

In some embodiments, the retinal projector 305 includes an illumination source (not shown in FIG. 3) based on one or more backlight units, one or more integrating spheres, some other sources, or combination thereof that can generate uniformly bright light. In one or more embodiments, the one or more backlight units within the retinal projector 305 comprise diffusers and brightness enhancement films. In one or more other embodiments, the one or more integrating spheres within the retinal projector 305 are made with diffusely scattering coatings or surfaces.

In some embodiments, light coupled into the backlight units or the integrating spheres of the retinal projector 305 can be emitted from LEDs, lasers, lamps, other types of light sources, or combination thereof, which may be integrated into the retinal projector 305. Wavelengths of light emitted from the light sources integrated into the retinal projector 305 can be in the visible spectrum (e.g., wavelengths between approximately 390 nm and 700 nm), or in the infrared spectrum (e.g., wavelengths between approximately 700 nm and 1 mm). In general, the wavelengths of light emitted from the retinal projector 350 can be tuned to match sensitivity of a detector of the retinal imaging device 310 (not shown in FIG. 3A) or sensitivity of the eye 220. In an embodiment, the light sources of the retinal projector 305 can be pulsed-based light sources. Alternatively, the light sources of the retinal projector 305 can be continuous wave (CW) light sources. The retinal projector 305 may comprise one emitter or multiple emitters depending on, e.g., the system geometry and required light intensity.

In some embodiments, light coming out of the uniform illumination sources (e.g., backlight units, integrating spheres, etc.) of the retinal projector 305 can be used to illuminate a partially transparent display (not shown in FIG. 3A), e.g., a liquid crystal display, a digital micromirror device (DMD) array display, a liquid crystal on silicon (LCOS) display, etc. In one embodiment, the partially transparent display is integrated into the retinal projector 305. In another embodiment, the partially transparent display is located outside of the retinal projector 305. The partially transparent display may be electronically controlled (e.g., based on instructions from the controller 210) such that an amplitude of light transmitted through each pixel of the partially transparent display is individually modulated. Thus, the partially transparent display may represent a pixel-based (or pixelated) partially transparent display. In one or more embodiments, the location of the partially transparent display may be in a plane that is conjugate or quasi-conjugate to the retina 350 of the eye 220.

In some embodiments, spatial modulation of light emitted by the retinal projector 305 can be accomplished based on a partially transparent pixelated display system, e.g., an LCD panel, a DMD array display, a LCOS display, etc., which may be integrated into the retinal projector 305 or placed outside of the retinal projector 305. Intensity of portions of light passing through one or more pixels of the partially transparent pixelated display may be extinguished electronically, e.g., based on instructions from the controller 210. In some other embodiments, spatial modulation of light emitted by the retinal projector 305 can be accomplished by a specific aperture of the retinal projector 305 (not shown in FIG. 3A) made from non-transparent materials of suitable shape, e.g., circular, rectangular, square, etc. The aperture of the retinal projector 305 may be attached to, e.g., a robotic arm or a multi-axis translation stage, which may allow for the aperture to be moved in space along any space dimension, e.g., based on instructions from the controller 210. The spatial modulation of light emitted from the retinal projector 305 may be based on information about the estimated location of the pupil 225 of the eye 220 obtained from, e.g., the imaging device 365 of the eye tracking system 215. The information about estimated location of the pupil 225 may be passed from the eye tracking system 215 to the controller 210 that controls the spatial modulation of light emitted from the retinal projector 305.

In some embodiments, the methods presented herein for the spatial modulation of light emitted from the retinal projector 305 allows for at least a portion of the emitted light passing through a pupil plane to be transmitted to the eye 220. For example, by controlling locations of the transmissive pixels of the partially transparent pixelated display associated with the retinal projector 305 or by controlling location of the aperture of the retinal projector 305 (e.g., based on instructions from the controller 210), it can be ensured that spatial location of a beam entering the eye 220 is coincident with the location of the ocular pupil 335. In this way, an entire anterior surface of an eyeball of the eye 220 may not be bathed in light, which prevents unwanted scatter and stray light from going into the retinal imaging device 310.

In some embodiments, the retinal imaging device 310 includes a detector that may be implemented as an array of pixels (not shown in FIG. 3A), which captures images of rendered content on the retina 350 over a large field-of-view (e.g., 45 degrees). Additionally, the detector of the retinal imaging device 310 may be configured to operate at a relatively high frame (capture) rates. Support for a large field-of-view and high capture rates allow the retinal imaging device 310 to capture saccades of velocities, e.g., eye-movements of up to 400-600 degrees/sec or other large eye-movements.

Figure 3B:
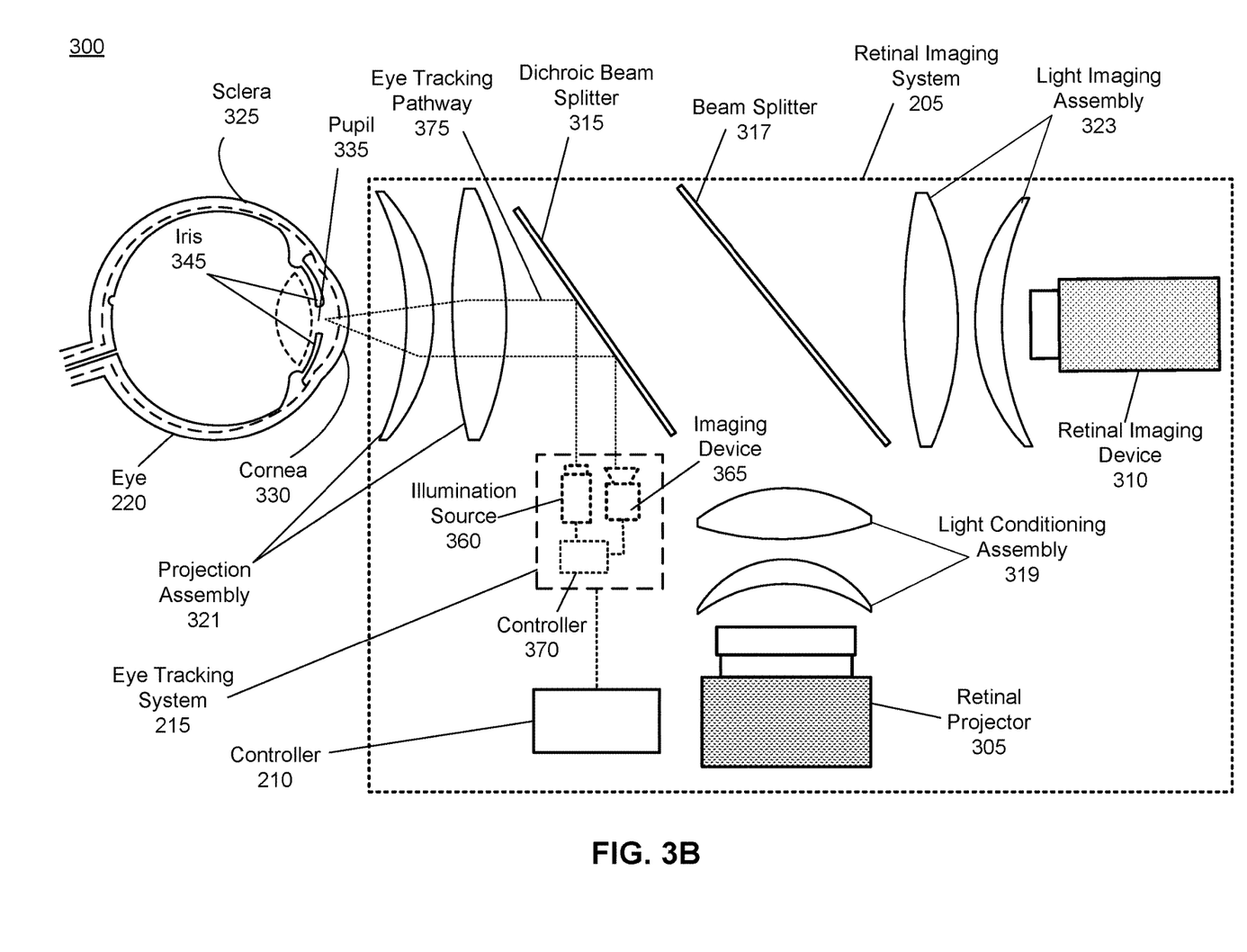
FIG. 3B illustrates an eye tracking pathway in the detailed diagram of the retinal imaging system in FIG. 3A, in accordance with one or more embodiments.

FIG. 3B illustrates an eye tracking pathway 375 in the detailed diagram 300 of the retinal imaging system 205 of FIG. 3A, in accordance with one or more embodiments. In one embodiment illustrated in FIG. 3B, light that propagates within the retinal imaging system 205 through the eye tracking pathway 375 originates from the illumination source 360 of the eye tracking system 215 under test, and the emitted light is then reflected from a surface (e.g., dichroic surface) of the beam splitter 315 and projected by the projection assembly 321 before reaching one or more surfaces of the eye 220. In an alternate embodiment (not shown in FIG. 3B), light that propagates within the retinal imaging system 205 through the eye tracking pathway 375 and illuminates the one or more surfaces of the eye 220 may be emitted from a display (not shown in FIG. 3B) incorporated into the retinal imaging system 205. As discussed above, the eye tracking system 215 under test may be configured to first estimate a location of the pupil 335 in the eye 220, and to provide information about the estimated location of the pupil 335 to the controller 210 of the retinal imaging system 205.

Due to the rotation and movement of the eye 220, the portion of the eye's surface illuminated by light propagating through the eye tracking pathway 375 may be variable. In some embodiments, the illumination source 360 (or the display of the retinal imaging system 205) projects light in a spectrum where the cornea 330 is nearly transparent (e.g., the near infrared or visible spectrum). In the case in which part of a light pattern (e.g., structured light pattern) passes through the cornea 330 and illuminates the iris 345, the resultant illumination pattern on the approximately planar interface of the iris 345 is distorted according to some optical power of the surface of the cornea 330. For the region within the pupil 335 of the iris 345, the intensity of the illumination pattern is significantly reduced. In some embodiments, the illumination pattern upon the pupil 335 is considered to be negligible. The controller 370 of the eye tracking system 215 under test may identify a distorted circular unilluminated portion in the image captured by the imaging device 365 as the pupil 335. The controller 370 may further estimate a position and angular orientation of the eye 220 based on the estimated location of the pupil 335. In an embodiment, the illumination source 360 (or the display of the retinal imaging system 205) includes multiple light sources that emit beams of light toward the eye 220, e.g., toward the surface of the cornea 330. The controller 370 can be configured to determine "glints" in images captured by the imaging device 365 corresponding to reflections of the light sources in the cornea 330. As the light sources are in known locations in the retinal imaging system 205, the controller 370 can infer a position and orientation of the eye 220, including estimated location of the pupil 335.

In one embodiment, the eye 220 is illuminated with a structured light pattern emitted from the illumination source 360 (or from the display of the retinal imaging system 205). In this case, the controller 370 can use certain location(s) of the reflected structured light pattern in an image captured by the imaging device 365 to estimate the location of the pupil 335. In another embodiment, the controller 370 estimates the location of the pupil 335 based on magnitudes of image light captured by the imaging device 365 over a plurality of time instants. The controller 370 may provide information about the estimated location of the pupil 335 to the controller 210, which is coupled to the eye tracking system 215 under test.

After estimating the location of the pupil 335, the eye tracking system 215 under test continues to track a position and orientation of the eye 220 in order to estimate one or more eye tracking parameters of the eye 220. For example, the controller 370 of the eye tracking system 215 under test can estimate values for the one or more eye tracking parameters, e.g., an angle of eye-gaze, a torsion of the eye 220, a shape of the eye 220, a current focal distance of the eye 220, a dilation of the pupil 335, IPD, other features of the eye's state, or some combination thereof. In one embodiment, the controller 210 may instruct the eye tracking system 215 under test to track a position and orientation of the eye 220 in a time period during which the retinal imaging system 205 determines the one or more eye tracking parameters. In this case, the retinal imaging system 205 and the eye tracking system 215 under test operate at different wavelengths of light. In alternate embodiments, the eye tracking system 215 under test can be configured (e.g., by the controller 210) to track a position and orientation of the eye 220 before or after determination of the one or more eye tracking parameters by the retinal imaging system 205, i.e., operations of the eye tracking system 215 under test and of the retinal imaging system 205 can be sequential.

In some embodiments, the illumination source 360 (or the display of the retinal imaging system 205) projects light propagating through the eye tracking pathway 375 in a spectrum where the cornea 330 is nearly opaque (e.g., infrared light with a wavelength greater than 1.5 μm) and the imaging device 365 (e.g., a long infrared camera) detects the resultant illumination pattern. When the cornea 330 is illuminated by the light pattern, the controller 370 may estimate the eye's angular orientation and/or translation based on the curvature of the cornea 330. Because the cornea 330 projects outward from the approximately ellipsoidal sclera 325, the controller 370 may estimate a position and orientation of the eye 220 by detecting the curvature of the cornea 330. The controller 370 may also estimate the eye's position and orientation by detecting the cornea-sclera interface, i.e., the roughly circular outline where the surface of the cornea 330 and the surface of the sclera 335 intersect. The controller 370 may also estimate the eye's position and orientation by detecting the vertex of the cornea 330, i.e., the part of the cornea 330 that extends furthest from the center of the eye 220. The controller 370 may provide the estimated values of the one or more eye tracking parameters to the controller 210 coupled to the eye tracking system 215 under test.

Figure 3C:
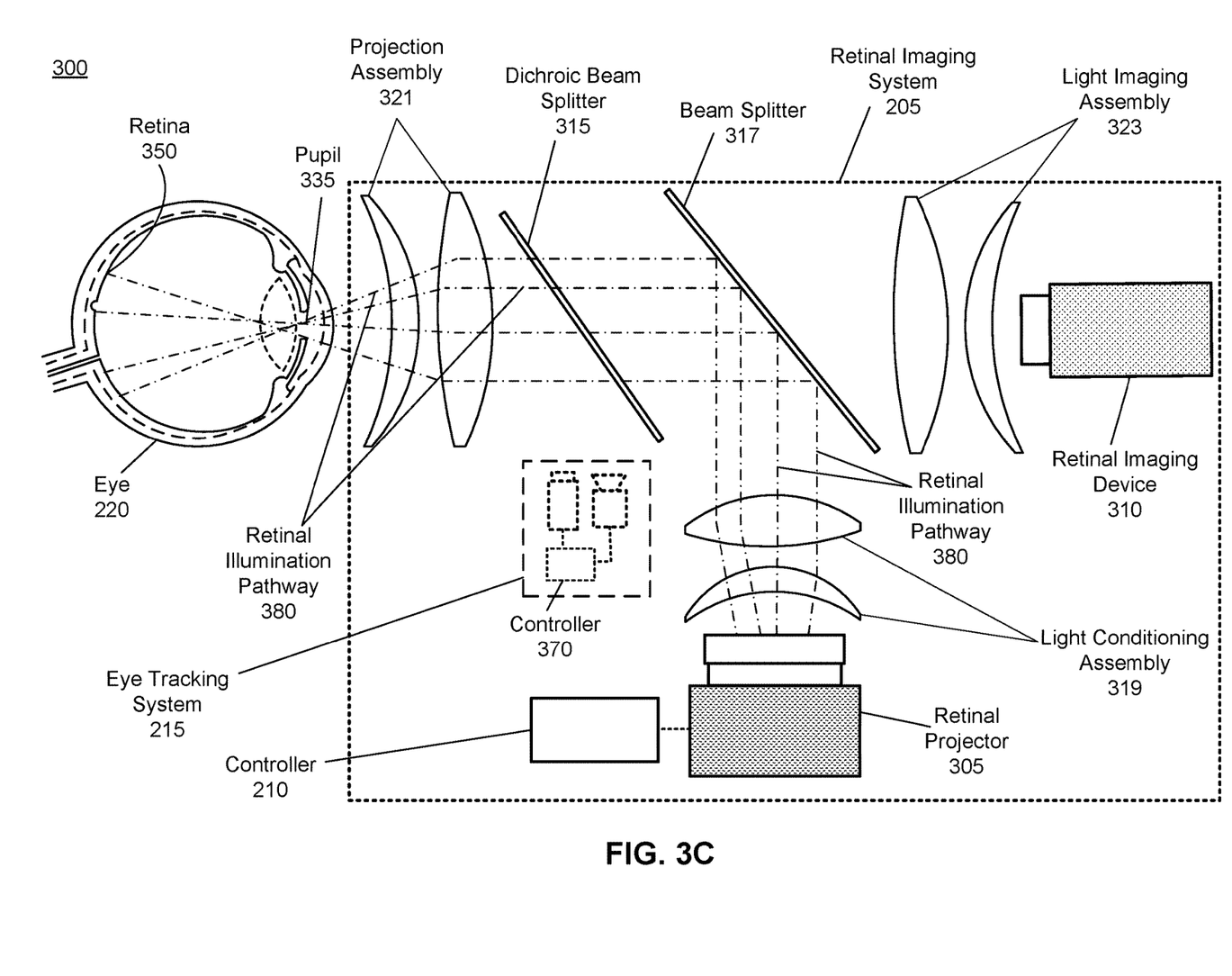
FIG. 3C illustrates a retinal illumination pathway in the detailed diagram of the retinal imaging system in FIG. 3A, in accordance with one or more embodiments.

FIG. 3C illustrates a retinal illumination pathway 380 in the detailed diagram 300 of the retinal imaging system 205 of FIG. 3A, in accordance with one or more embodiments. The retinal projector 305 emits a light pattern that propagates through the light conditioning assembly 319 and along the retinal illumination pathway 380 through the projection assembly 321 to be delivered to the pupil 335 of the eye 220. At least a portion of the light pattern delivered to the pupil 335 may reach the retina 350. In some embodiments, the light pattern emitted from the retinal projector 305 is rendered to be delivered to the pupil 335 based on the information about the estimated location of the pupil 335 obtained from the eye tracking system 215 under test. In one embodiment, the controller 210 coupled to the eye tracking system 215 under test is configured to obtain the information about the estimated location of the pupil 335 from the controller 370 of the eye tracking system 215 under test. The controller 210 may provide the obtained information about the location of the pupil 335 to an illumination source (not shown in FIG. 3C) of the retinal projector 305. As shown in FIG. 3C, the retinal projector 305 and the light conditioning assembly 319 are positioned outside of a primary display optical path of the eye 220. Therefore, to be delivered to the pupil 335 of the eye 220, the light pattern emitted from the retinal projector 305 and conditioned by the light conditioning assembly 319 is reflected from a surface of the beam splitter 317 and projected by the projection assembly 321 toward the pupil 335.

In some embodiments, as discussed, the retinal projector 305 includes a spatial light modulator (not shown in FIG. 3C) coupled to the illumination source. The spatial light modulator may be based on a partially transparent pixelated display system, e.g., an LCD panel, a DMD array display, a LCOS display, etc., which may be integrated into the retinal projector 305. Alternatively, the spatial light modulator may be based on a specific aperture of the retinal projector 305 made from non-transparent materials of suitable shape attached to, e.g., a robotic arm or a multi-axis translation stage, which may allow for the aperture to be moved in space along any space dimension. The spatial light modulator spatially modulates light that propagates through the light conditioning assembly 319 and along the retinal illumination pathway 380 and through the projection assembly 321 to be delivered to the pupil 335. At least a portion of the spatially modulated light pattern may reach the retina 350. The emitted light pattern may be spatially modulated based on the information about the estimated location of the pupil 335 obtained from the eye tracking system 215 under test. By spatially modulating the emitted light pattern, the spatial light modulator of the retinal projector 305 controls amplitudes of light within an eye-box of the eye 220.

In some embodiments, as discussed, the illumination source of the retinal projector 305 includes a plurality of emitters, e.g., a 2D array of LEDs, or a 2D array of VCSELs. Stimulus presentation to the retina 350 is limited by the level of addressability of individual LEDs/VCSELs in the 2D array. In one embodiment, the controller 210 of the retinal imaging system 205 is configured to individually control each LED/VCSEL in the retinal projector 305. In this way, a low level stimulus can be delivered to the pupil 335 and further to the retina 350 of the eye 220.

Figure 3D:
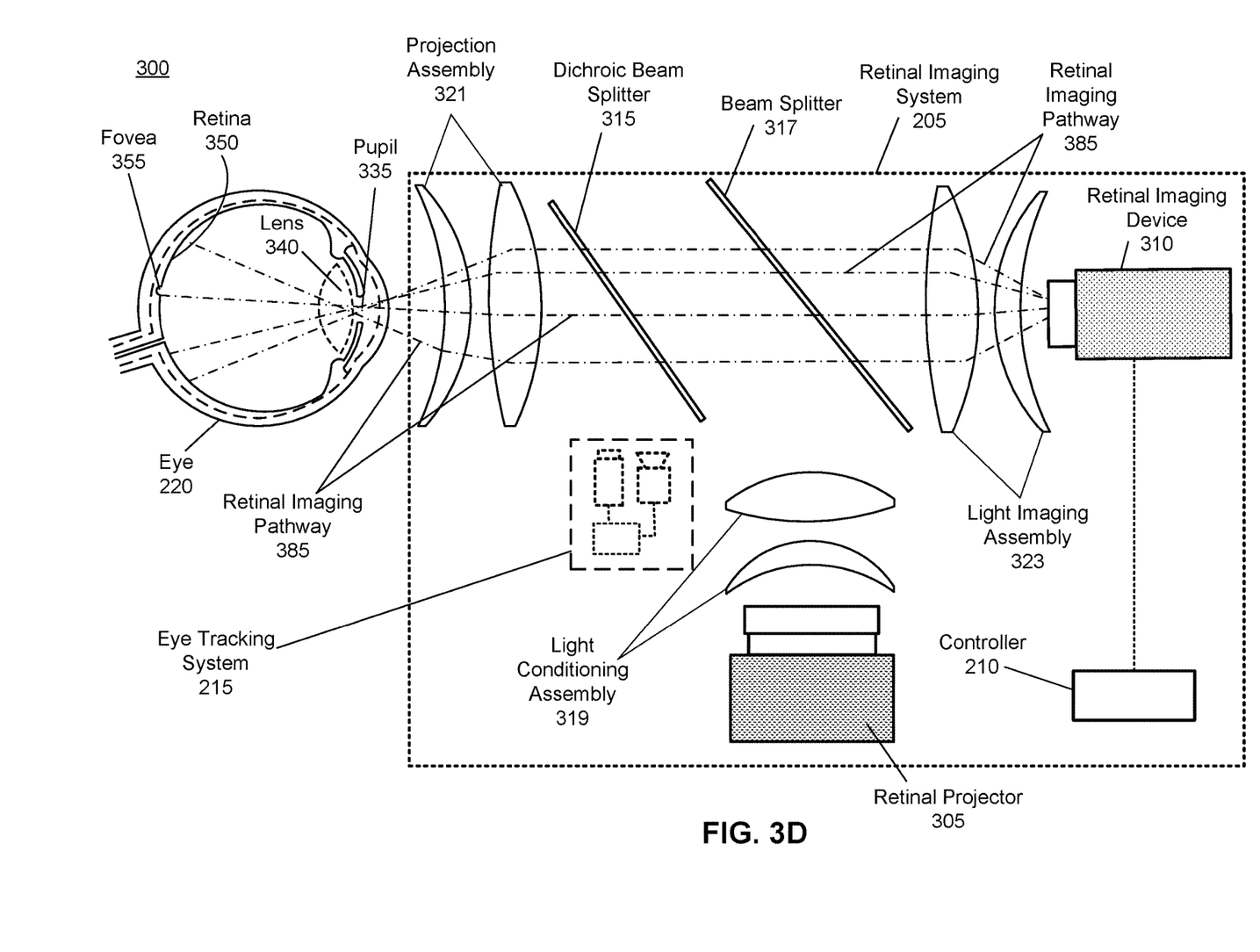
FIG. 3D illustrates a retinal imaging pathway in the detailed diagram of the retinal imaging system in FIG. 3A, in accordance with one or more embodiments.

FIG. 3D illustrates a retinal imaging pathway 385 in the detailed diagram 300 of the retinal imaging system 205 of FIG. 3A, in accordance with one or more embodiments. Light that propagates along the retinal imaging pathway 385 is projected by the projection assembly 321 to pass through the pupil 335 and the lens 340 to reach the retina 350, including the fovea 355 of the eye 220. After reaching the retina 350, light is then reflected from the retina 350 and propagates through the retinal imaging system 205 along the retinal imaging pathway 385 back to the light imaging assembly 323 to be captured by the retinal imaging device 310. In some embodiments, as discussed, the retinal imaging device 310 includes a detector that may be implemented as an array of pixels (not shown in FIG. 3D), which captures one or more images of rendered content on the retina 350 over a large field-of-view (e.g., 45 degrees).

As shown in FIG. 3D, the controller 210 may be coupled to the retinal imaging device 310. The controller 210 can be configured to determine one or more eye tracking parameters related to the eye 220, based on the captured one or more images of the retina 350. The controller 210 determines the "ground truth" for the one or more eye tracking parameters, such as an angle of eye-gaze, a torsion of the eye 220, a shape of the eye 220, a current focal distance of the eye 220, a dilation of the pupil 335, IPD, other features of the eye's state, or some combination thereof. The controller 210 compares the estimated values for the one or more eye tracking parameters obtained from the eye tracking system 215 under test with the one or more eye tracking parameters determined based on the one or more images of the retina 350 captured by the retinal imaging device 310. Based on the comparison between the estimated values and the determined values (i.e., "ground truth" values) for the one or more eye tracking parameters, the controller 210 can characterize performance of the eye tracking system 215 under test. Once performance of the eye tracking system 215 under test is characterized, the eye tracking system 215 under test may be incorporated into a HMD, e.g., the HMD 100 in FIG. 1. In some embodiments, the controller 210 evaluates a difference between each individual estimated value of the eye tracking parameters and each individual determined value of the eye tracking parameters. In this way, for each eye tracking parameter, the controller 210 computes an error value between a "ground truth" value of the eye tracking parameter determined by the retinal imaging system 205 and an estimated value of the eye tracking parameter obtained by the eye tracking system 215 under test. In an embodiment, based on error values associated with the eye tracking parameters, the retinal imaging system 205 can generate a report that presents characterization results of the eye tracking system 215 under test to an administrator. The report can, e.g., flag results for one or more eye tracking parameters that do not meet pre-determined specification.

Figure 4:
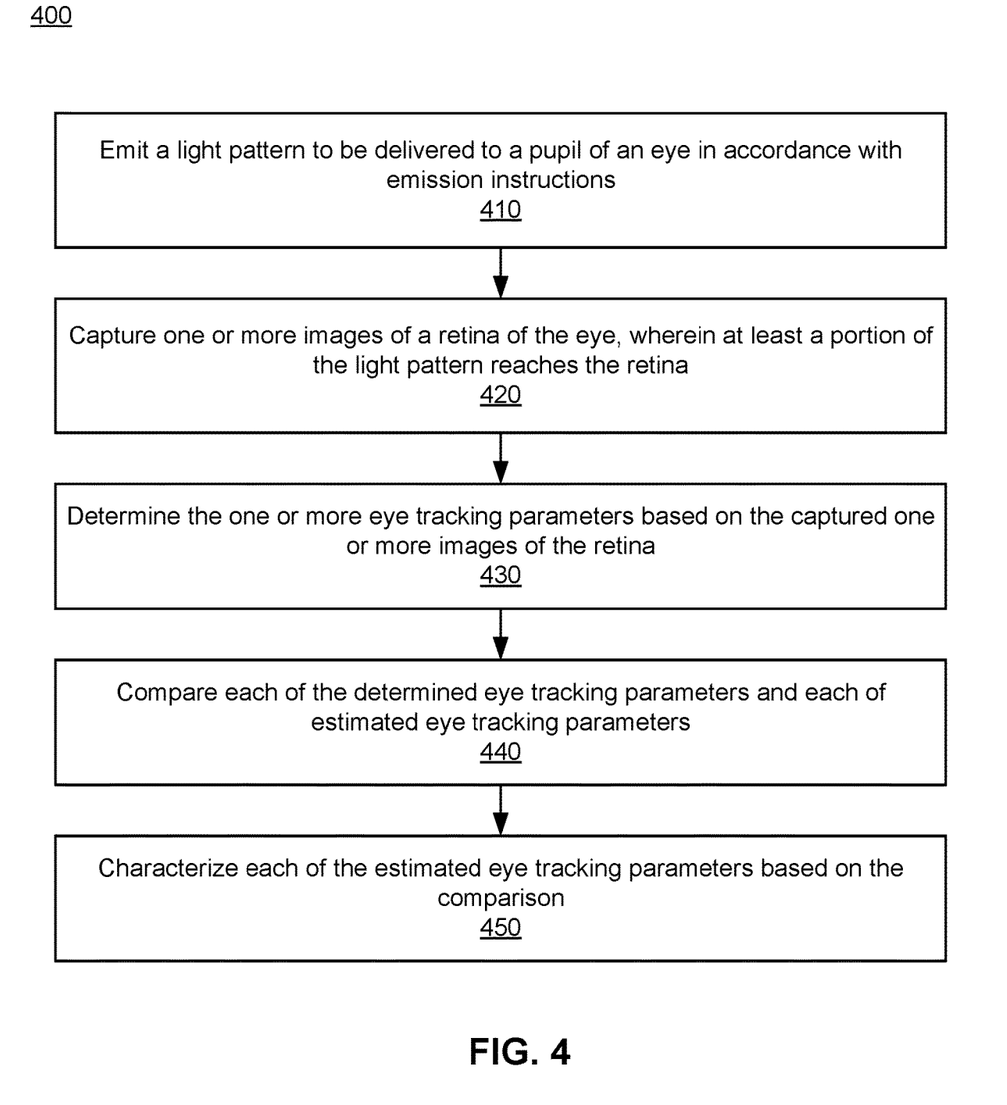
FIG. 4 is a flow chart illustrating a process of characterizing performance of an eye tracking system under test using a retinal imaging system, the eye tracking system under test may be later incorporated into the HMD shown in FIG. 1, in accordance with one or more embodiments.

FIG. 4 is a flow chart illustrating a process 400 of characterizing performance of an eye tracking system under test, which may be placed into a retinal imaging system, e.g., the retinal imaging system 205 shown in FIGS. 3A-3D, in accordance with one or more embodiments. The eye tracking system under test may be later incorporated into a HMD, e.g., the HMD 100 shown in FIG. 1. The process 400 of FIG. 4 may be performed by the components of the retinal imaging system 205. Other entities may perform some or all of the steps of the process in other embodiments. Likewise, embodiments may include different and/or additional steps, or perform the steps in different orders.

The retinal imaging system emits 410 (e.g., via a projector) a light pattern to be delivered to a pupil of an eye in accordance with emission instructions. A location of the pupil may be estimated by an eye tracking system under test and provided to the retinal imaging system (e.g., a controller). The emission instructions (e.g., generated by the controller) may include information about the estimated location of the pupil. At least a portion of the emitted light pattern that is delivered to the pupil may reach a retina of the eye, including a fovea. In some embodiment, the emitted light pattern is spatially modulated, based on the information about the estimated location of the pupil.

The retinal imaging system captures 420 (e.g., via an imaging device) one or more images of a retina of the eye, wherein at least the portion of the light pattern reaches the retina. In some embodiments, the retinal imaging system captures 420 the one or more images of rendered content on the retina over a relatively large field-of-view and at a relatively high capture rates. In some embodiments, the light pattern comprises a structured light pattern. The retinal imaging system may capture the one or more images of rendered content on the retina by capturing one or more images of at least a portion of the structured light pattern reaching the retina.

The retinal imaging system determines 430 (e.g., via a controller) one or more eye tracking parameters based on the captured one or more images of the retina. The retinal imaging system determines 430 the "ground truth" for values of the one or more eye tracking parameters, based on the captured one or more images of rendered content on the retina. For example, the eye tracking parameters include an angle of eye-gaze, a translation of the eye, a torsion of the eye, a shape of the eye, a current focal distance of the eye, a dilation of the pupil, IPD, an accommodation of the eye, other features of the eye's state, or some combination thereof. In some embodiments, retinal imaging system determines the one or more eye tracking parameters based in part on the captured one or more images of at least the portion of the structured light pattern.

After estimating the location of the pupil, the eye tracking system under test continues tracking a position and orientation of the eye to estimate the one or more eye tracking parameters. In one embodiment, the operations 410, 420, 430 of the retinal imaging system can be executed in a time period during which the eye tracking system under test estimates values for the one or more eye tracking parameters. In this case, the retinal imaging system and the eye tracking system under test operate at different wavelengths of light. In alternate embodiments, the operations 410, 420, 430 of the retinal imaging system can be executed before or after the eye tracking system under test estimating values for the one or more eye tracking parameters. The eye tracking system under test may illuminate various surfaces of the eye with a light pattern and captures light reflected from the various surfaces of the eye. The eye tracking system under test may estimate the eye's angular orientation and/or translation based on a curvature of the eye's cornea. The eye tracking system under test may also estimate the eye's position and orientation by detecting a cornea-sclera interface. The eye tracking system under test may also estimate the eye's position and orientation by detecting a vertex of the cornea.

The retinal imaging system compares 440 (e.g., via the controller) each of the determined eye tracking parameters with each of the estimated eye tracking parameters. In some embodiments, the retinal imaging system calculates a difference between each of the determined one or more eye tracking parameters and each of the estimated one or more eye tracking parameters. Based on the difference, the retinal imaging system determine a quality value for each of the estimated one or more eye tracking parameters, the quality value indicating how close each estimated eye tracking parameter is to a corresponding determined eye tracking parameter.

The retinal imaging system characterizes 450 (e.g., via the controller) each of the estimated eye tracking parameters based on the calculated differences. The retinal imaging system indicates acceptability for each of the estimated eye tracking parameters, based on quality values for the estimated eye tracking parameters obtained from the calculated differences. For example, if a quality value indicates that a difference between an estimated value of eye tracking parameter and a corresponding determined eye tracking parameter is within an acceptable range, the retinal imaging system indicates that the estimated eye tracking parameter is acceptable. If the quality value indicates that the estimated eye tracking parameter deviates from the corresponding determined eye tracking parameter more or less than an associated threshold, the retinal imaging system indicates the estimated eye tracking parameter is not acceptable, i.e., the estimated eye tracking parameter fails. In another example, the retinal imaging system may generate a report and provide the report to the user based on the calculated differences. Once the eye tracking system under test is characterized and all the eye tracking parameters are acceptable, the eye tracking system under test may be incorporated (fabricated) into a HMD system.

Additional Configuration Information

The foregoing description of the embodiments of the disclosure has been presented for the purpose of illustration;

it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A method performed by a retinal imaging system to assess function of an eye tracking system, the method comprising:
   capturing one or more images of a retina of an eye;
   receiving, from the eye tracking system, a location of a pupil of the eye estimated by the eye tracking system;
   generating, based on the location of the pupil of the eye, an instruction signal for spatial modulation of light emitted from the retinal imaging system toward the retina;
   determining, by the retinal imaging system, one or more eye tracking parameters for the eye, comprising a gaze direction of the eye, using the captured one or more images of the retina while the eye tracking system estimates the one or more eye tracking parameters for the eye, comprising the gaze direction of the eye;
   comparing the one or more eye tracking parameters determined by the retinal imaging system with the one or more eye tracking parameters estimated by the eye tracking system; and
   outputting an indication of the function of the eye tracking system based on a result of the comparison.

2. The method of claim 1, further comprising:
   determining the one or more eye tracking parameters within a time period during which the eye tracking system estimates the one or more eye tracking parameters.

3. The method of claim 2, wherein at least one wavelength of a light pattern emitted from the retinal imaging system toward the retina is different than at least one other wavelength of light emitted from the eye tracking system toward the eye during the time period.

4. The method of claim 1, further comprising:
   determining the one or more eye tracking parameters within a first time period different than a second time period during which the eye tracking system estimates the one or more eye tracking parameters.

5. The method of claim 1, further comprising:
   spatially modulating the light emitted from an illumination source of the retinal imaging system toward the eye, based on the instruction signal.

6. The method of claim 1, further comprising:
   calculating a difference between each of the one or more eye tracking parameters determined by the retinal imaging system and a corresponding eye tracking parameter of the one or more eye tracking parameters estimated by the eye tracking system;
   determining a quality value for the corresponding eye tracking parameter based on the difference; and
   indicating acceptability for the corresponding eye tracking parameter based on the determined quality value.

7. The method of claim 1, further comprising:
   capturing the one or more images of the retina by capturing one image of a structured light pattern that reaches the retina; and
   determining the one or more eye tracking parameters using the at least one captured image.

8. The method of claim 1, further comprising:
   providing emission instructions that include the instruction signal to a two-dimensional array of light emitting diodes of the retinal imaging system; and
   emitting, by the two-dimensional array of light emitting diodes, a light pattern toward the retina in accordance with the emission instructions.

9. The method of claim 1, further comprising:
   providing emission instructions that include the instruction signal to a two-dimensional array of vertical-cavity surface-emitting lasers of the retinal imaging system; and
   emitting, by the two-dimensional array of vertical-cavity surface-emitting lasers, a light pattern toward the retina in accordance with the emission instructions.

10. The method of claim 1, wherein the one or more eye tracking parameters further comprise at least one of: an angle of eye-gaze for the eye, a torsion of the eye, a shape of the eye, a focal distance of the eye, a dilation of the pupil, an inter-pupillary distance associated with the eye, a translation of the eye, and an accommodation of the eye.

11. The method of claim 1, further comprising:
instructing an illumination source of the retinal imaging system to emit a light pattern;
conditioning the light pattern by a light conditioning assembly of the retinal imaging system;
reflecting, by a beam splitter of the retinal imaging system, at least a portion of the conditioned light pattern; and
projecting, by a projection assembly of the retinal imaging system, the reflected portion of the conditioned light pattern toward the pupil.

12. The method of claim 1, wherein the eye tracking system is incorporated into a head-mounted display after the one or more eye tracking parameters are determined to be acceptable based on the comparison.

13. A retinal imaging system to assess function of an eye tracking system, comprising:
a processor; and
a memory storing instructions that, when executed by the processor, cause the processor to:
receive, from the eye tracking system, a location of a pupil of an eye estimated by the eye tracking system;
generate a modulation signal based on the location of the pupil of the eye;
modulate light emitted from the retinal imaging system using the modulation signal toward a retina of the eye;
capture one or more images of the retina;
determine one or more eye tracking parameters, comprising a gaze direction of the eye, using the captured one or more images of the retina while the eye tracking system estimates the one or more eye tracking parameters, comprising the gaze direction of the eye;
compare the one or more eye tracking parameters determined by the processor of the retinal imaging system with the one or more eye tracking parameters estimated by the eye tracking system; and
output an indication of the function of the eye tracking system based on a result of the comparison.

14. The retinal imaging system of claim 13, wherein the instructions further cause the processor to:
determine the one or more eye tracking parameters within a time period during which the eye tracking system estimates the one or more eye tracking parameters,
wherein a first spectrum of a light pattern emitted from the retinal imaging system toward the retina is different than a second spectrum of light emitted from the eye tracking system toward the eye during the time period.

15. The retinal imaging system of claim 13, wherein the instructions further cause the processor to:
calculate a difference between each of the one or more eye tracking parameters determined by the retinal imaging system and a corresponding eye tracking parameter of the one or more eye tracking parameters estimated by the eye tracking system;
determine a quality value for the corresponding eye tracking parameter based on the difference; and
generate an acceptability report for the eye tracking system based at least in part on the determined quality value.

16. The retinal imaging system of claim 13, wherein the instructions further cause the processor to:
include the eye tracking system into a head-mounted display, based on the generated acceptability report.

17. A non-transitory computer-readable storage medium storing instructions that when executed by a processor, cause the processor to;
instruct a retinal imaging system to capture one or more images of a retina of an eye;
instruct the retinal imaging system to receive, from an eye tracking system a location of a pupil of the eye estimated by the eye tracking system;
generate, based on the location of the pupil of the eye, an instruction signal for spatial modulation of light emitted from the retinal imaging system toward the retina;
determine one or more eye tracking parameters, comprising a gaze direction of the eyes, using the captured one or more images of the retina while the eye tracking system estimates the one or more eye tracking parameters, comprising the gaze direction of the eye;
compare the determined one or more eye tracking parameters with the one or more eye tracking parameters estimated by the eye tracking system; and
generate an indication of acceptability of the eye tracking system based on a result of the comparison.

18. The non-transitory computer-readable storage medium of claim 17, wherein the instructions further cause the processor to:
determine the one or more eye tracking parameters within a time period during which the eye tracking system estimates the one or more eye tracking parameters.

19. The non-transitory computer-readable storage medium of claim 17, wherein the instructions further cause the processor to:
instruct the retinal imaging system to spatially modulate the light emitted from an illumination source of the retinal imaging system, based on the instruction signal.

20. The non-transitory computer-readable storage medium of claim 17, wherein the instructions further cause the processor to:
calculate a difference between each of the one or more eye tracking parameters and a corresponding eye tracking parameter of the one or more eye tracking parameters estimated by the eye tracking system;
determine a quality value for the corresponding eye tracking parameter based on the difference; and
instruct the retinal imaging system to indicate the acceptability for the corresponding eye tracking parameter, based on the determined quality value.

* * * * *